United States Patent [19]

Tyler

[11] 4,339,327
[45] Jul. 13, 1982

[54] MINIATURE SLAB GEL ELECTROPHORESIS SYSTEM

[76] Inventor: Jonathan M. Tyler, 9126 116th St., Edmonton, Alberta, T6G-1P9, Canada

[21] Appl. No.: 256,898

[22] Filed: Apr. 23, 1981

[51] Int. Cl.[3] .............................................. B01D 13/02
[52] U.S. Cl. ................................................. 204/299 R
[58] Field of Search ........................ 204/180 G, 299 R; 23/230 B

[56] References Cited

U.S. PATENT DOCUMENTS

| | | | |
|---|---|---|---|
| 3,719,580 | 3/1973 | Roberts et al. | 204/180 G X |
| 3,901,782 | 8/1975 | Vadasz et al. | 204/180 G |
| 3,932,265 | 1/1976 | Hoefer | 204/180 G X |

*Primary Examiner*—Howard S. Williams

[57] ABSTRACT

An electrophoresis system for separating organic molecules comprising a base, an electrophoresis tank mounted on the base, and electrical outlets mounted on the base connected to the tank and an external electrical power source. The electrophoresis tank includes a back plate mounted perpendicular to the base, the back plate having an upper reservoir adapted to receive a buffer fluid, a lower reservoir mounted on the base adjacent the back plate adapted to receive the fluid, a pair of sample plates having a layer of gel therebetween releasably mounted to the back plate, a plate clamping bar adjustably mounted on and parallel to the back plate adapted to retain and maintain the sample plates adjacent and parallel to the back plate, the layer of gel being adapted to permit the migration of the organic molecules contained in the gel layer upon application of an electric field from the power source.

18 Claims, 3 Drawing Figures

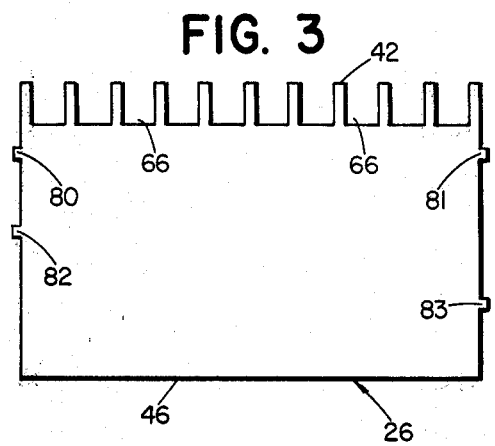
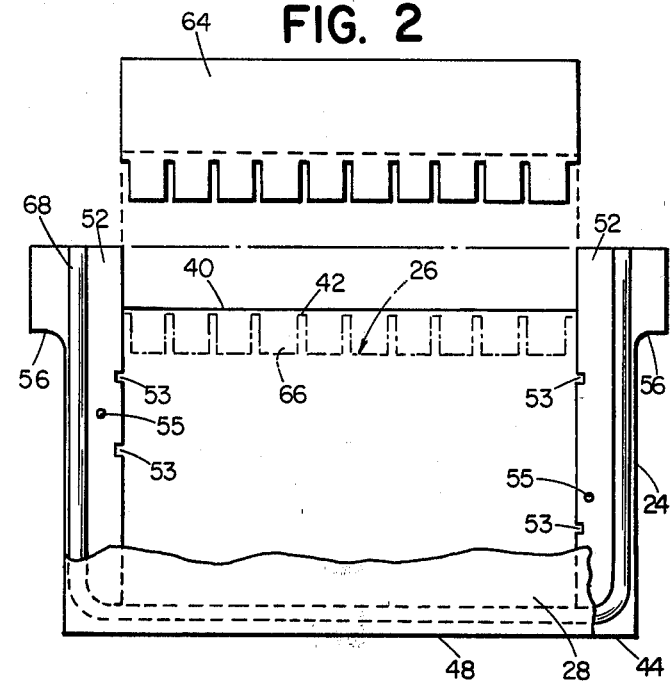
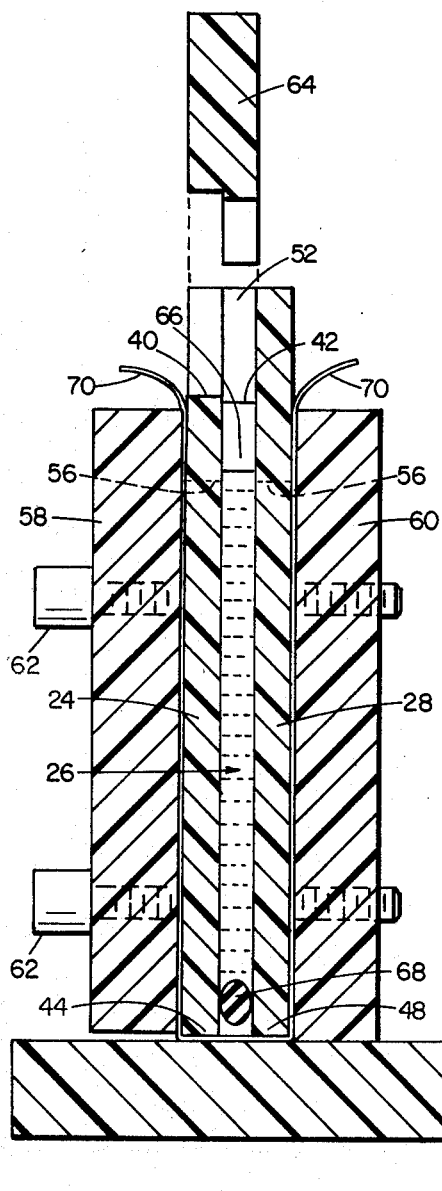

MINIATURE SLAB GEL ELECTROPHORESIS SYSTEM

FIELD OF THE INVENTION

This invention relates to electrophoresis systems for separating organic molecules and, more particularly, to novel miniature slab gel electrophoresis systems.

BACKGROUND OF THE INVENTION

Electrophoresis systems which employ the zone electrophoresis method of separating proteins, polypeptides, nucleic acids or other organic molecules with electrical charge to determine their quantities and molecular weights are common in the prior art. Sample components of these organic molecules, supported on stabilizing media, are separated by an electric field on the basis of differences in net charge, size and shape. The separation takes place at a constant pH and ionic strength. Polyacrylamide gel, agarose, cellulose or granulated gels are commonly used as stabilizing media, these gels being porous compounds through which the sample components can migrate in an electric field. The electric field applied to the gel causes samples to migrate through the gel.

DNA (deoxyribonucleic acid), for example, which is negatively charged, moves toward the positive electrode; smaller fragments of DNA migrate faster through the gel than do larger fragments. A gradient of DNA sizes is thus established, and the individual size classes may be detected by reacting with ethidium bromide and examining the gel in ultraviolet light. In contrast, proteins may have net negative or positive charges, and therefore migrate unpredictably. For polypeptides, they are first reacted with the detergent sodium dodecyl sulfate (SDS) to cover them with a uniform net negative charge. The resultant complex is then electrophoresed in a gel which also contains SDS. Individual classes of polypeptides are thus separated on the basis of molecular weight—the smaller polypeptides can penetrate the pores in the gel more readily than the larger ones, and a gradient of molecular weights is established. The polypeptides can then be observed by reacting the gels with various protein-specific stains.

These electrophoresis systems can also employ the isoelectric focussing method, a variant of electrophoresis. In this method, a pH gradient is first established electrophoretically by using an isoelectric focussing gel such as a gel containing ampholenes. After the establishment of such a gradient, samples such as polypeptides are then placed on the gel and they migrate to their respective isoelectric points on the pH gradient. Again, the locations of these samples on the gel are observed by using the various protein-specific stains.

Although these systems are satisfactory in their use, they are expensive and composed of many parts. They are also bulky and cumbersome and difficult to transport to remote non-laboratory working sites. Moreover, their time-consuming procedures require approximately three days to produce the laboratory results.

SUMMARY OF THE INVENTION

In view of such deficiencies in the prior art, it is a major object of the present invention to provide a novel slab gel electrophoresis system which is composed of few parts.

It is another object of the present invention to provide a novel slab gel electrophoresis system which is small in size, light in weight, and easily transportable to remote working sites.

It is a further object of the present invention to provide a novel slab gel electrophoresis system which is capable of producing high quality laboratory results quickly, and which requires use of but very small amounts of extremely expensive reagents such as acrylamide and ampholenes.

In order to accomplish the above and still further objects, the present invention provides a novel electrophoresis system for separating organic molecules. The system comprises a base, an electrophoresis tank mounted on the base, and electrical outlets mounted on the base which are connected to the tank and an external electrical power source.

More particularly, the electrophoresis tank includes a back plate mounted perpendicular to the base, a lower reservoir mounted on the base, a pair of sample plates having a layer of gel therebetween releasably mounted to the back plate, and a plate clamping bar adjustably mounted on and parallel to the back plate.

The back plate has an upper reservoir which is adapted to receive a buffer fluid, the upper reservoir being connected to one of the electrical outlets. The lower reservoir mounted on the base adjacent the back plate is similarly adapted to receive the fluid, the lower reservoir being similarly connected to another of the electrical outlets.

The pair of sample plates are releasably mounted to the back plate and parallel thereto, the sample plates having heights which are less than the height of the back plate. The sample plate adjacent the back plate has, in at least its central portion, a height which is less than the second sample plate; and the upper end of this plate cooperates with the back plate to define the front of the upper reservoir so as to permit the fluid in the reservoir to contact the upper end of the layer of gel between the sample plates. The lower ends of the sample plates are immersed in the fluid of the lower reservoir to permit the fluid to contact the lower end of the layer of gel. The layer of gel is adapted to permit migration of the organic molecules contained in the gel layer upon application of an electric field from the power source.

The plate clamping bar is adjustably mounted, at its ends, on and parallel to the back plate, the clamping bar being adapted to retain and maintain the sample plates between the bar and the back plate, whereby the fluids in both the upper and lower reservoirs are in contact with the layer of gel to permit migration of the organic molecules.

In the preferred embodiment, the novel slab gel electrophoresis system further includes side spacers which are mounted between the sample plates to provide constant gel thickness, gel layer positioning slots in the side spacers to prevent slippage of the gel layer from the sample plates, and sample plate positioning pins which are also mounted perpendicular to the sample plates to provide accurate positioning thereof and to prevent the slippage of one sample plate with respect to another. In addition, a gasket seal is mounted between the back plate and the first sample plate to prevent the leakage of stabilizing chemicals from the layer of gel and the fluid in the upper reservoir. Curvilineal extensions which extend from the sides of the sample plates allow the sample plates to rest atop screws of the plate clamping bar and position the plates accurately.

The system in the preferred embodiment still further includes a pair of compression plates which are spaced from the electrophoresis tank and mounted perpendicular to the base. The compression plates are adapted to receive the gel plates having the layer of gel therebetween and to compress the layer of gel into uniform thickness. The system in the preferred embodiment further includes a comb-like die which is adapted to be mounted atop the layer of gel to form teeth-like grooves therein, each of the grooves being adapted to receive one sample of the organic molecules.

Other objects, features, and advantages of the present invention will appear from the following detailed description of a preferred embodiment thereof, taken together with the accompanying drawing.

DESCRIPTION OF THE PREFERRED EMBODIMENT

FIG. 1 is a side cross section view of the novel slab gel electrophoresis system of the present invention;

FIG. 2 is a front view of the gel plates, and the comb-like die of the electrophoresis system of the present invention; and FIG. 3 is a front view of the layer of gel of FIG. 2, with grooves formed therein by the die.

Referring to the drawings, the electrophoresis system of the present invention, generally designated 12, comprises a base 14, an electrophoresis tank 16 mounted on base 14, and electrical outlets 18 mounted on base 14 which are connected to tank 16 and an external electrical power source.

More particularly, electrophoresis tank 16, manufactured from clear acrylic plastic, includes a back plate 20 mounted perpendicular to base 14, a lower reservoir 22 mounted on base 14, a pair of sample plates 24 and 28 having a layer of gel 26 therebetween releasably mounted to back plate 20, and a plate clamping bar 30 adjustably mounted on and parallel to back plate 20.

A recess in back plate 20, together with sample plate 24, define an upper reservoir 32 which receives an electrode buffer fluid 34 and contains a 32-gauge platinum electrode 36 which in turn is connected to one of the electrical outlets 18. Lower reservoir 22 which is mounted on base 14 adjacent back plate 20 similarly receives fluid 34 and contains another 32-gauge platinum electrode 38 which in turn is connected to another of the electrical outlets 18.

The pair of sample plates 24 and 28 is releasably mounted parallel to back plate 20, plates 24 and 28 having heights which are less than the height of back plate 20. Each of sample plates 24, 28 has a generally rectangular central portion with curvilineal extensions 56 or "ears" projecting from the opposite sides thereof. The central portion of inner sample plate 24 has a height which is less than the height of the central portion of outer sample plate 28, and inner plate 24 is mounted adjacent to back plate 20 with the upper edge 40 of its central portion extending partially up the height of the reservoir 32 in back plate 20 to permit fluid 34 in upper reservoir 32 to flow into the gap between plates 24, 28 and cover the upper end 42 of gel layer 26, thereby permitting the migration of organic molecules in gel layer 26. The lower ends 44 and 48 of sample plates 24 and 28, respectively, are immersed in fluid 34 of lower reservoir 22 to permit fluid 34 therein to contact lower end 46 of gel layer 26. Curvilineal extensions 56 extend from the tops of the sides of sample plates 24 and 28, as best shown in FIG. 2, and rest atop screws 50 of the opposite ends of plate clamping bar 30 to position plates 24 and 28 accurately vertically so that when so aligned, the lower edges of plates 24 and 28, and of the extensions 56, are aligned.

Plate clamping bar 30 of brass is adjustably mounted on and parallel to back plate 20; bar 30 retains and maintains sample plates 24 and 28 adjacent and parallel to back plate 20. Four stainless steel cap screws 50, two at each end of bar 30, are used to force bar 30 toward back plate 20, thereby in turn forcing sample plates 24 and 28 to be adjacent and parallel to back plate 20. Having both upper end 42 and lower end 46 of gel layer 26 immersed in fluid 34 in reservoirs 20, 22, permits migration of the organic molecules contained in the gel layer.

In the preferred embodiment, the novel electrophoresis system 12 further includes sample plate side spacers 52, gel layer positioning slots 53, sample plate positioning pins 55, gasket seal 54, and sample plate extensions 56. As best shown in FIG. 2, a pair of 1.5 mm wide side spacers 52 are mounted perpendicular to sample plates 24 and 28 to provide constant gel thickness. Side spacers 52 include gel layer positioning slots 53 which are used to prevent slippage of gel layer 26 from sample plates 24, 28. Slots 53 facilitate the creation of gel layer orientation extensions 80, 81, 82, 83 which are then used to distinguish the orientation of gel layer 26 once it is removed from plates 24, 28. As best shown in FIG. 3, the orientation of gel layer 26, whether it is facing up or down, can be easily determined because extensions 80, 82 are more closely spaced than are extensions 81, 83. Sample plate positioning pins 55 of stainless steel, mounted perpendicular to and extending through sample plates 24 and 28, provide accurate positioning of sample plates 24, 28 and prevent the slippage of one sample plate with respect to another.

In addition, silicone rubber tank gasket 54, positioned below reservoir 32 and between back plate 20 and inner sample plate 24, seals in stabilizing chemicals in fluid 34 and gel layer 26.

The preferred embodiment still further includes a pair of compression plates 58, 60, also of clear acrylic, which are spaced from electrophoresis tank 16 and mounted perpendicular to base 14. Compression plates 58 and 60 are used to receive sample plates 24 and 28 and to compress the gel layer 26 therebetween into uniform thickness. Four stainless steel screws 62 are used to force plates 58 and 60 together in compressing sample plates 24 and 28.

The system in the preferred embodiment further includes a comb-like die 64 of acrylic, as best shown in FIGS. 1 and 2, which is mounted atop gel layer 26 to form teeth-like grooves 66 therein, each of grooves 66 being adapted to receive one sample of the organic molecules.

In use, sample plates 24 and 28 are first assembled and sealed by placing clear silicone rubber gasket 68 around side spacers 52 of plates 24 and 28, as best shown in FIG. 2. Sample plate positioning pins 55 permit accurate and reproducible positioning of plates 24, 28 and also prevent the slippage of plates 24, 28 with respect to one another. A liner of conventional plastic wrap 70, as best shown in FIG. 1, is placed around the lower edges 44 and 48 of plates 24 and 28, respectively. Plates 24 and 28 are then slipped into compression plates 58 and 60, as best shown in FIG. 1. Screws 62 are then tightened to compress sample plates 24 and 28 to create a space therebetween of 1.5 millimeters in thickness. A solution of gel is poured into the space between spacers 52 of plates 24 and 28. Plastic liner 70 is now used to prevent any excess of gel 26 that might be spilled during pouring from polymerizing between gel plates 24, 28 and compression plates 58, 60.

The parallel compression plates 58, 60 and spacers 52 together create a gel of constant thickness, preventing the common occurence of bowed or lens-shaped gel in conventional clamping devices. Before placing die 64 atop gel layer 26, die 64 is lightly sprayed with silicone in order to siliconize the region between adjacent grooves 66 when they are formed, thereby facilitating the removal of die 64. Die 64 is then placed atop gel layer 26, as best shown in FIG. 1, to produce grooves 66 therein, each of which is adapted to receive a sample of the organic molecules, as best shown in FIG. 3.

When gel layer 26 has polymerized, die 64, plastic wrap 70, and gasket 68 are removed and sample plates 24 and 28 having gel layer 26 therebetween are placed into electrophoresis tank 16. Gel layer positioning slots 53 now prevent the polymerized gel layer 26 from slipping through sample plates 24, 28. Curvilineal extensions 56, the lower edge of which rest on screws 50, position sample plates 24, 28 accurately during every experiment, as best shown in FIG. 1. Cap screws 50 are tightened over clamping bar 30 to maintain sample plates 24 and 28 parallel to back plate 28, thereby maintaining gel layer 26 at its constant thickness. In addition, clamping bar 30 is vertically positioned so that its top edge is below grooves 66 in gel layer 26, thereby allowing an experimenter to view the various samples placed in the grooves. Approximately 50 milliliters of electrode buffer fluid 34 are poured into both upper and lower reservoirs 32 and 22, immersing the upper and lower ends 42 and 46, respectively, of gel layer 26. Gasket seal 54 prevents the leakage of stabilizing chemicals in fluid 34 directly from upper reservoir 32 to lower reservoir 22, thereby allowing these chemicals to function in gel layer 26.

One sample of the organic molecules is placed into one groove 66 of gel layer 26. The electrophoresis system is run at approximately 15 to 50 milli-Amperes, corresponding to a voltage of 30 to 80 volts DC for approximately 60 minutes. At the completion of this electrophoretic treatment, gel layer 26 is removed from sample plates 24 and 28, as best shown in FIG. 3, and stained and destained by using conventional methods to produce the electrophoresis image. Gel layer orientation extensions 80, 81, 82, 83 permit the experimenter to distinguish the orientation of gel layer 26 once it is removed from plates 24, 28. Because gel layer 26 is transparent, it is often difficult to determine the correct orientation—whether gel layer 26 is being viewed from the front or the back. As best shown in FIG. 3, the orientation of gel layer 26 can now be easily determined because extensions 80, 82 are spaced closer apart than extensions 81, 83. The total time required to complete one set of runs is approximately three hours.

What is claimed is:

1. An electrophoresis system for separating organic molecules, comprising
    a base
    an electrophoresis tank mounted on said base, and
    a pair of electrodes adapted for connection to an external electrical power source
    said electrophoresis tank including
    a back plate mounted on said base perpendicular thereto, said back plate having an upper reservoir adapted to receive fluid, one of said electrodes being disposed in said upper reservoir,
    a lower reservoir mounted on said base adjacent said back plate adapted to receive said fluid, the other of said electrodes being disposed in said lower reservoir,
    a pair of sample plates adapted to have a layer of gel therebetween releasably mounted to said back plate and parallel thereto, said sample plates having heights less than that of said back plate,
    a first of said sample plates having a height less than a second of said plates is mounted adjacent to said back plate, the upper end of said first sample plate cooperating therewith for receiving said fluid in said upper reservoir and allowing said fluid to contact a said layer of gel,
    the lower ends of said sample plates are immersed in said fluid of said lower reservoir for allowing said fluid to contact a said layer of gel,
    a plate clamping bar adjustably mounted on and parallel to said back plate, said clamping bar being adapted to retain and maintain said sample plates adjacent and parallel to said back plate,
    said layer of gel being adapted to permit migration of said organic molecules contained therein upon application of an electric field from said power source, and
    whereby fluids in both said upper and lower reservoirs will be in contact with a said layer of gel to permit migration of said organic molecules contained in said gel layer.

2. The electrophoresis system as claimed in claim 1, further comprising
    side spacers mounted intermediate said sample plates adjacent the ends thereof to provide a constant gap therebetween, each of said spacers being attached to one of said sample plates.

3. The electrophoresis system as claimed in claim 2, wherein
    said side spacers include gel layer positioning slots in the inwardly-facing sides thereof, said slots serving to create gel layer orientation extensions on said gel layer to prevent slippage of said gel layer, slots at one side of said plates being offset vertically relative to the slots at the opposite side of said plates.

4. The electrophoresis system as claimed in claim 1, further comprising
    sample plate positioning pins mounted perpendicular to and extending between said sample plates to provide accurate positioning and to prevent slippage of said sample plates.

5. The electrophoresis system as claimed in claim 1, further comprising
    a gasket seal mounted between said back plate and said first sample plate to prevent the leakage of stabilizing chemicals from said layer of gel and said fluid in said upper reservoir, said seal comprising silicone tubing.

6. The electrophoresis system as claimed in claim 1, further comprising
    curvilineal extensions extending from the opposite sides of said sample plates, said extensions being positioned so that the lower edges of the extensions on one of said plates are aligned with the lower edges of the extensions of the other of said plates when the lower edges of said plates are in alignment whereby said extensions position said sample plates accurately.

7. The electrophoresis system as claimed in claim 1, further comprising
a pair of gel compression plates spaced from said electrophoresis tank and mounted on said base perpendicular thereto, said compression plates being adapted to receive said sample plates having a layer of gel therebetween and one of said plates being movable under pressure towards the other of said plates to compress a layer of gel between sample plates into uniform thickness.

8. The electrophoresis system as claimed in claim 7, further comprising
a comb-like die adapted for mounting atop a said layer of gel to form teeth-like grooves therein, the portion of said die forming said grooves being a predetermined thickness equal to the desired thickness of said layer of gel and projecting downwardly from an upper and thicker portion of said die, said upper and thicker portion being arranged to rest upon and engage the top of a said sample plate, each of said grooves being adapted to receive one sample of said organic molecules.

9. An electrophoresis system for separating organic molecules, said system comprising:
a pair of sample plates adapted for receiving a layer of gel therebetween;
means for mounting said sample plates in generally vertical, parallel spaced-apart relationship with a layer of gel therebetween;
upper and lower reservoirs each adapted to receive fluid and having therein a respective electrode;
said lower reservoir being adapted to receive the lower ends of said sample plates therewithin whereby fluid in said lower reservoir will contact a lower portion of a layer of gel between said sample plates,
one of said sample plates having in at least its central portion a height less than the other of said sample plates and defining at least a portion of a side of said upper reservoir whereby fluid in said upper reservoir will contact an upper portion of a layer of gel between said sample plates.

10. The system of claim 9 including spacers at the opposite sides of said sample plates for maintaining a predetermined spacing between said sample plates, each of said spacers being attached to one of said sample plates.

11. The system of claim 10 including a plurality of slots in said spacers, each of said slots being arranged to extend from the gap between said sample plates towards the exterior of the respective one of said spacers defining said slot, and there being a plurality of slots at each side of said sample plates.

12. The system of claim 11 wherein a slot at one side of said sample plate is offset relative to the slots at the other side of said sample plates.

13. The system of claim 9 including pins extending between and locating said sample plates relative to each other.

14. The system of claim 9 wherein each of said sample plates includes a tab projecting outwardly from each side edge thereof, said tabs being arranged to engage said means for mounting said sample plates to locate said sample plates vertically relative to said reservoirs.

15. The system of claim 9 wherein said means for mounting said sample plates includes a generally vertical back plate and a plate clamping bar secured to its ends to said back plate, said sample plate being disposed intermediate said back plate and said clamping bar, said lower reservoir being adjacent the bottom of said back plate, and said upper reservoir being adjacent to and in part defined by an upper portion of said back plate.

16. The system of claim 9 or claim 15 wherein each of said sample plates includes a generally rectangular central portion and a curvilineal extension projecting outwardly from the opposite sides of said central portion, said curvilineal extensions of said plates being arranged such that the bottoms of said plates are aligned with each other when said curvilineal extensions of one of said plates are in face-to-face alignment with the extensions of the other of said plates, and said means for mounting said sample plates includes means for engaging the undersides of said curvilineal extensions.

17. The system of claim 9 wherein said means for mounting said sample plates and said upper and lower reservoirs are mounted on a base and said system includes, mounted on said base and spaced from said means and said reservoirs, a pair of compression plates having generally vertical facing planar compression surfaces, one of said plates being attached to said base and the other of said plates being mounted in face-to-face relationship with said one plate and being movable under pressure towards said one plate, whereby when said sample plates with gel therebetween are mounted between said compression surfaces of said compression plates said layer of gel will be compressed into a layer of uniform thickness.

18. The electrophoresis system as claimed in claim 7 or 17 further comprising
a gasket seal mounted between said sample plates to prevent the leakage of any of said gel from said layer during said compression of said gel into uniform thickness, said seal comprising silicone tubing.

* * * * *